United States Patent [19]

Shinitzky

[11] Patent Number: 5,582,831
[45] Date of Patent: Dec. 10, 1996

[54] ANTI-TUMOR VACCINES

[75] Inventor: Meir Shinitzky, Rehovot, Israel

[73] Assignee: Yeda Research and Development Co., Ltd., Israel

[21] Appl. No.: 217,086

[22] Filed: Mar. 25, 1994

Related U.S. Application Data

[63] Continuation of Ser. No. 108,764, Aug. 21, 1993, abandoned, which is a continuation of Ser. No. 798,142, Nov. 26, 1991, abandoned.

[51] Int. Cl.$^6$ .................. A61K 39/395; A61K 39/00; A61K 39/38; A61K 39/40; A61K 39/42; A61K 39/44
[52] U.S. Cl. .................. 424/277.1; 424/184.1; 424/174.1; 424/179.1; 424/181.1
[58] Field of Search .................. 424/184.1, 174.1, 424/277.1, 179.1, 181.1

[56] References Cited

U.S. PATENT DOCUMENTS

| | | |
|---|---|---|
| 4,634,590 | 1/1987 | Cohen et al. . |
| 4,902,288 | 2/1990 | Ingram .................. 424/85.1 |
| 4,931,275 | 6/1990 | Shinitzky et al. .................. 424/88 |
| 4,996,194 | 2/1991 | Cohen et al. . |

OTHER PUBLICATIONS

Siemann. In: Rodent Tumor Models in Experimental Cancer Therapy. ed. Kallman. pp. 12–15. Pergamon Press.
Fareed et al "Human Tumor Regression–Associated Antigenic Determinants" Human Tumor Antigens and Specific Tumor Therapy, 1989, Alan R Liss Inc, NY. pp. 317–334.
Cysyk et al "Protein Cross–Linking Properties of the Antitumor Agent Inosine Dialdehyde" Cancer Treatment reports 60(5) May 1976, pp. 563–570.
Shinitzky; "Membrane Fluidity in Malignancy—Adversative and Recuperative"; Bioch. et. Biophys. Acta, 738(1984) 251–261.
Lider et al.; "Therapeutic Vaccination Against Adjuvant Arthritis Using Autoimmune T Cells Treated with Hydrostatic Pressure"; Proc. Natl. Acad. Sci. USA, 84, pp. 4577–4580, Jul. 1987.
Ramakrishna et al., "Potentiation of Delayed–Type Hypersensitivity Response to Syngeneic Tumors in Mice Prevaccinated with Cells Modified by Hydrostatic Pressure and Crosslinking"; Can. Immunol. Immunother., 33 (1991) 1–8.
Richert et al., "Promotion of Tumor Antigenicity in EL–4 Leukemia Cells by Hydrostatic Pressure"; Can. Immunol. Immunother, 22 (1986) 119–124.
Lider et al., "Vaccination Against Experimental Autoimmune Diseases Using T Lymphocytes Treated with Hydrostatic Pressure"; Ann. N.Y. Acad. Sci., 475 (1986) 267–273.
Skornick et al., "Active Immunotherapy of Human Solid Tumor with Autologous Cells Treated with Cholesteryl Hemisuccinate"; Cancer, 58, No. 3(1986) 650–654.

*Primary Examiner*—James C. Housel
*Assistant Examiner*—N. M. Minnifield
*Attorney, Agent, or Firm*—Morgan & Finnegan, L.L.P.

[57] ABSTRACT

An immunogen derived from modified tumor cells and capable of inducing an anti-tumor immune response is prepared in accordance with the invention by exposing tumor cells to a crosslinking agent, which is a 2',3'-nucleoside or nucleotide dialdehyde at a concentration and for a time sufficient to cause crosslinking of proteins in the cells' plasma membranes. Improved immunogenicity may be obtained if the cells are also exposed to hydrostatic pressure at a level and for a time sufficient to cause displacement of the proteins in the cells' plasma membranes. Exposure of the tumor cells to the crosslinking agent and to hydrostatic pressure at the same time is a preferable method of producing the immunogen. The immunogen is suitable for use as an anti-tumor vaccine for inducing an anti-tumor immune response in cancer patients.

44 Claims, 6 Drawing Sheets

5,582,831

ANTI-TUMOR VACCINES

This is a continuation of U.S. application Ser. No. 08/108,764, filed on Aug. 21, 1993, abandoned, which is a continuation of U.S. application Ser. No. 07/798,142, filed on Nov. 26, 1991, abandoned.

FIELD OF THE INVENTION

The present invention is generally in the field of cancer therapy and concerns novel immunogens, anti-tumor vaccines for use in human and veterinary medicine comprising them, process for the preparation of said immunogens, and methods for anti-tumor vaccination.

The immunogens of the present invention are derived from tumor cells which were treated to increase their specific immunogenicity which immunogen may be such cells, plasma membranes of such cells or tumor-specific immunogenic proteins obtained from such cells or membranes.

BACKGROUND OF THE INVENTION AND PRIOR ART

As is well known and documented, cancer cells generally contain on their external surface specific neo-antigens which are foreign to the host body. Nevertheless, for reasons which are not entirely clear, the immune system fails to develop an effective immune reaction against the tumor cells. Attempts have been made to immunize cancer patients with preparations that will stimulate their immune systems to develop a reaction against the neo-antigens with the hope that such an immune reaction will destroy the residing cancer.

U.S. Pat. No. 4,931,275 discloses anti-tumor vaccines which contain as active ingredient tumor cells which have been treated to augment their immunogenic properties, their plasma membranes or specific membrane proteins obtained from these cells or membranes. The treatment which augments their immunogenicity in accordance with this patent consists of either treatment with cholesteryl hemisuccinate which rigidifies the lipid layer of the plasma membrane or by the application of hydrostatic pressure up to about 1500 atm, or a combination of the two treatments.

SUMMARY OF THE INVENTION

It is an object of the present invention to provide a novel immunogen capable of inducing an anti-tumor immune response. More specifically, it is an object of the present invention to provide such an immunogen which is derived from modified tumor cells, which may be such cells, membranes thereof or immunogenic proteins obtained from said cells or membranes.

It is another object of the present invention to provide a process for preparing said immunogen.

It is a further object of the present invention to provide a vaccine comprising said immunogen.

It is a still further object of the present invention to provide a method of treating a tumor comprising immunizing of a tumor patient with such an anti-tumor vaccine.

GENERAL DESCRIPTION OF THE INVENTION

In accordance with the present invention it was found, that the immunogenicity of an immunogen derived from treated tumor cells maybe augmented by exposing tumor cells to the crosslinking action of a crosslinking agent being a 2',3'-nucleoside or nucleotide dialdehyde (hereinafter "said crosslinking agent").

Additionally, it was found in accordance with the present invention that the tumor specific immunogenicity can be augmented by subjecting the cells to a combined treatment of exposure to both said crosslinking agent and to hydrostatic pressure. It was furthermore found that this immunogenicity can be augmented even further if the exposure to said crosslinking agent and to hydrostatic pressure is done simultaneously.

By one of its aspects the present invention provides an immunogen derived from modified tumor cells and capable of inducing an anti-tumor immune response, wherein said modified tumor cells have been prepared by exposing tumor cells to said crosslinking agent at a concentration and for a time sufficient to cause crosslinking of proteins in the cell's plasma membranes.

By a preferred embodiment of the present invention, said modified tumor cells are prepared by exposing tumor cells to both said crosslinking agent and to hydrostatic pressure at a level and for a time sufficient to cause displacement of proteins in the cell's plasma membranes.

By a more preferred embodiment of the present invention, the exposure to said crosslinking agent and to hydrostatic pressure is done simultaneously.

The concentration of said crosslinking agent is preferably above about 20 mM.

The hydrostatic pressure is preferably within the range of about 1200–1400 atm. Surprisingly, pressure above 1500 yields an immunogen having a far inferior anti-cancer immunization potency. The application and release of pressure is preferably gradual, e.g. over a period of 5–10 minutes.

Said crosslinking agent is preferably a 2',3'-dialdehyde of a natural nucleotide or nucleoside as non-naturally occurring, i.e. synthetic nucleosides or nucleotides are very often highly toxic.

The preferred crosslinking agents are represented by the following formula I:

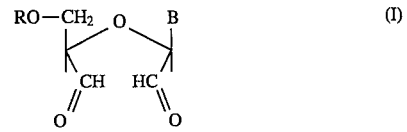

wherein

R is H, or a mono-, di- or tri-phosphate group, and

B is a nucleotide base selected from the group consisting of adenine, guanine, cytosine, thymine and uracil.

Examples of such a crosslinking agent are 2',3'-adenosine dialdehyde (AdA) and 2',3'-adenosine adenoxine monophosphate dialdehyde (AMPdA).

The compound of formula I may be prepared by reacting a nucleoside or a nucleotide of the following formula II:

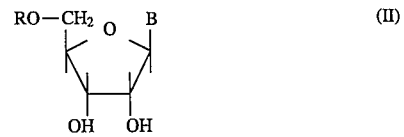

wherein R and B have the meanings given above for formula I, with an oxidizing agent, e.g. an alkali periodate.

The immunogen may consist of the whole modified tumor cells, membranes derived from such cells, as well as proteinaceous material obtained from such cells or membranes which substantially retains the capability of the modified tumor cells to induce the anti-tumor immune response.

Preferably, after the treatment in accordance with the invention, the modified tumor cells are exposed to high intensity radiation in order to destroy their genetic material. This is particularly important where the whole modified tumor cells are used for immunization and may not necessarily be required where said immunogen consists of membrane preparations or said proteinaceous substances.

By another aspect, the present invention provides a process for preparing an immunogen derived from modified tumor cells and capable of inducing an anti-tumor immune response, said process comprising the steps of:

a) providing tumor cells;

b) incubating the cells with said crosslinking agent at a concentration and for a time sufficient to obtain crosslinking between membrane proteins; and c) separating between the tumor cells and said crosslinking agent.

The above process preferably comprises also exposing the tumor cells to hydrostatic pressure at a level and for a time sufficient to cause displacement of proteins in the plasma membranes of the cells. The hydrostatic pressure is preferably applied during the incubation step of the cells with said crosslinking agent (step b).

Where the desired immunogen consists of the whole modified tumor cells, the product of the above process may be used per se or after several purification treatments, e.g. consisting of centrifugation and removal of the supernatant.

Where the preparation consists of membranes of such modified tumor cells, the modified tumor cells are subjected to further treatment in which the cells are disrupted, e.g. by exposure to a hypotonic medium or by sonication, and then the membrane fragments are collected e.g. by centrifugation in a sucrose gradient, as generally known per se.

Where the desired immunogen consists of said proteinaceous material, the whole modified cells or the plasma membranes are subjected to further treatment consisting for example of dissolving the membranes by the use of detergents, separating the proteinaceous material by one of various methods known per se, e.g. gel filtration, and then determining which of the separated proteinaceous material fragments possesses the desired immunogenicity.

Said immunogen may be used for the immunization of cancer patients against their tumor or may be used for the sensitization of immune cells in vitro. For immunization, said immunogen may be injected into a patient together with a pharmaceutically acceptable carrier or adjuvant in an amount sufficient to achieve anti-cancer immune response.

For in vitro sensitization, immune cells, i.e. leukocytes or lymphocytes, are withdrawn from the patient by means known per se and then cultured together with said immunogen until a population of such immune cells reactive against said immunogen is obtained. Said population may then be reinjected into a cancer patient in order to treat his tumor.

By another of its aspects, the present invention thus provides a vaccine composition comprising said immunogen and a pharmaceutically acceptable carrier.

By a still further aspect, the present invention provides a method of treatment of cancer comprising injecting a cancer patient with said immunogen or with the sensitized immune cells.

While the immunization of patients in accordance with the present invention can be performed by the use of an allogenic immunogen, it is preferably performed by the use of an autologous immunogen. The use of an autologous immunogen entails significant advantages in that the immune response which occurs is primarily directed against the neo-antigen of the tumor, while where an allogenic immunogen is used the resulting immune response will be against all the non-self antigens of such an immunogen. The use of an autologous immunogen has the further advantage in that the neo-antigens associated with a specific tumor may differ from one patient to another. Where an autologous preparation is used, the method comprises the steps of:

a) withdrawing tumor growth from a patient by biopsy or surgery;

b) dissociating intact tumor cells by mechanical or enzymatic means;

c) dispersing the cells in a medium;

d) incubating the cells with 2',3'-adenosine dialdehyde (AdA) in a concentration and for a time sufficient to cause crosslinking of proteins in the cell's plasma membrane;

e) removing the AdA and preparing a tumor-specific immunogen derived from the modified cells obtained; and f) injecting said immunogen into the patient, whereby an anti-tumor immune response in said patient is induced.

Where an allogenic immunogen is being used, an immunogen derived from modified tumor cells obtained from a defined tumor cell line may be used.

BRIEF DESCRIPTION OF THE DRAWINGS

In the following, reference will at times be made to the accompanying drawings in which:

FIG. 7a: fluorescence results using anti-class I ($K^b+D^b$) antibody; FIG. 7b: fluorescence results using anti-B16 antibody;

EXAMPLES

Figure 1A:
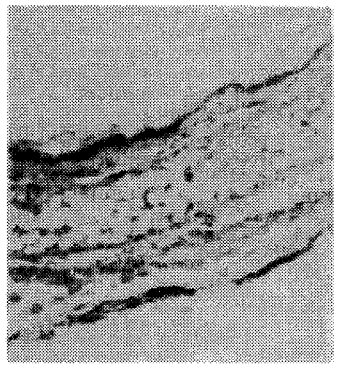
FIGS. 1a–1e histology of the delayed-type hypersensitivity reaction (DTH) in the ear of mice challenged with $10^5$ irradiated syngeneic EL4 leukemia cells in the ear following priming with an immunogenic preparation: a. unprimed; b. primed with unmodified EL4 cells; c. primed with AdA treated EL4 cells; d. primed with pressure treated EL4 cells; and e. primed with AdA and hydrostatic pressure treated EL4 cells.

The invention will now be illustrated with reference to the following non-limiting examples.

Example 1

Experimental Methods

Cells

Cells from an EL4 tumor, which is a chemically induced T-leukemia (Gorrer, 1961. In: Harris RJG, ed., Biological Approach to Cancer Chemotherapy. Academic Press, New York) were maintained in ascites form in the peritoneal cavity of 6–8-week old C57B1/6J female mice. About $10^5$ cells were inoculated i.p. and 10 days later the cells (approximately $5 \times 10^8$ cells per animal) were harvested.

Cells of ARadLV 136, which is a radiation-induced leukemogenic variant of ARadLV, were maintained in vitro as described previously (Haran-Ghera et al., 1977, J. Immunol. 118:600).

Adenosine 2',3'-dialdehyde (AdA)

AdA, which is a biologically compatible chemical crosslinker, was synthesized by a modification of the procedure previously described (Hansske et al., 1974, Bioorg. Chem. 3: 367): Adenosine (Sigma Chemical Co., St. Louis, Mo.) and sodium metaperiodate (Fluka Chemie AG, Buchs. FRG) were mixed in 100 ml aqueous solution to a final concentration of 10 mM of each of these substances, stirred in the dark and cooled with ice water for 1 h, and then concentrated to 5 ml in vacuum at 30° C. The resulting concentrate was then incubated for 12 h at 4° C. and the crystalline product which was obtained was separated and found to be homogeneous in thin-layer chromatography (silica gel G plate, 0.2 mm thickness, Merck Darmstadt; running solvent; acetonitrile/water, 4: 1 v/v, $R_F$ 0.80). The crystals were filtered, washed three times with cold water and dried over silica gel in vacuum (12 mm Hg; 1.6 kPa).

The yield of the above preparation procedure was found to be approximately 90%. The obtained product had a melting point of 110° C. and melting was accompanied by decomposition, this being in agreement with previous reports (Hansske et al., 1974, supra).

Modification of tumor cells

After harvesting, the cells were washed twice with PBS (pH 7.4) and then subjected to one of the following modification treatments. The viability of the modified tumor cells was assessed by trypan blue dye exclusion.

Modification I: crosslinking of proteins on tumor cell surface. About $10^8$ cells/ml were inoculated into a 50 ml tube (Falcon, Becton Dickinson Labware, N.J.) holding a PBS solution containing 0.5% AdA and were incubated in this solution for 1 h at room temperature with occasional mixing. Unbound AdA was removed by three cycles of centrifugation at 1500 rpm for 5 min, followed by gentle resuspending of the pellet in PBS (in the final resuspension PBS was added to obtain a desired cell concentration).

Modification II: application of hydrostatic pressure. This modification was performed in a similar manner as previously described (Richerr et al., 1986, Cancer Immunol. Immunother. 22:119). Cells were dispersed in PBS at a concentration of $10^8$ cells/ml in a capped Eppendorf plastic tube (1.5 ml, Netheler and Hinz GmbH, Hamburg, FRG) and filled to the brim. A 0.5 in. (1.27 cm) 18G needle, was inserted through the cap and served as a vent for pressure equalization. Both the needle and the tube were filled with PBS and the cap was pressed down without entrapping any air bubbles, (Removal of all air bubbles is important as these may cause cell disruption upon release of pressure). The tubes were then placed inside a pressure bomb of 40 ml capacity (Aminco, American Instruments Co., Md.), filled with PBS and sealed.

Pressure was gradually applied to reach a level of about 1200 atm within 7–8 min and this pressure was maintained for about 15 min. Thereafter, the bomb was unlocked and allowed to decompress gradually to ambient pressure in about 8–10 min. The cells were then transferred into a 50 ml tube in 10 ml PBS and centrifuged at 1500 rpm for 5 min. The pellet was then gently resuspended in PBS to the desired concentration.

Modification III: hydrostatic pressure and crosslinking in sequence. Cells were pressurized and then immediately crosslinked by the two modification procedures outlined above.

Modification IV: hydrostatic pressure and crosslinking simultaneously. Cells were pressurized and crosslinked at the same time by the two modification treatments described above.

Delayed-type hypersensitivity (DTH) assay

The DTH response was measured by skin reaction in the ear as hitherto described (Vadas et al., 1975. Int. Arch. Allergy Appl. Immunol. 49:670). For vaccination, unmodified or modified tumor cells were irradiated (10,000 rad) and then injected i.p. into C57BL/6J female mice at a dose of $10^7$ viable cells in 1 ml PBS/mouse (counts were determined before irradiation). After 8 days, vaccination was repeated as above with a fresh batch of unmodified or modified tumor cells.

A sample of $10^5$ unmodified and irradiated tumor cells (an empirically determined optimal dose) in 10 μl PBS was injected intradermally 8 days later in the right ear (0.5 in., 1.27 cm, 30G needle, Becton Dickinson, N.J.). The left ear (control ear) was injected with 10 μl PBS. After 10 h the mice were injected i.p. with 0.1 ml of a 1.0 mM 5-fluoro-2'-deoxyuridine (FdUrd, Sigma) solution and 30 min later injected with 2 μCi 5-$^{125}$I-labeled 2'-deoxyuridine ($^{125}$IdUrdR, sp. act. 5 Ci/ng, Amersham, UK) into the lateral tail vein.

Mice were sacrificed after 24 h from the time of challenge with tumor cells. The ears were then cut out carefully at the rims and the amount of radioactivity determined in a gamma counter (Gammamatic, Kontron). The results were expressed as the ratio of radioactivity in the right ear to that in the left ear (R/L $^{125}$IdUrd index). Five mice were included in each group. Control groups included unprimed mice, as well as those primed with unmodified tumor cells.

Histology of the ear

For histological purposes, the ears were fixed with Bouin's fixative for 48 h at room temperature. Excess fixative was removed thereafter by extensive washing with 70% ethanol. Any hair present was carefully shaved off and the ears were cut to uniform size for embedding and subsequent sectioning on a rotary microtome (Spencer model No. 820; American Optical Co.). The slides were stained with eosin and in some cases with toluidine blue (Vadas et al., 1975. supra)

$^{51}$Chromium-release cytotoxicity assay

The 5 h cytotoxicity assay was carried out as hitherto described (Brunner et al., 1976. In: Bloom and David, eds., supra). Briefly, EL4 as well as ARadLV 136 target cells were washed once in RPMI-1640 medium and the supernatant was aspirated to leave 0.1 ml with the cell pellet. The pellet was gently dispersed and resuspended in PBS with 5% fetal calf serum and centrifuged at low speed (1000 rpm for 5 min). 0.1 ml Na$_2$$^{51}$CrO$_4$ solution (Amersham, UK; 1 mCi/ml, sp. act. 200 mCi/mg) per 2×10$^6$ target cells was added to the pellet in 0.1 ml buffer and the suspension was gently vortexed. Incubation was done in small petri dishes in a humidified incubator, flushed with 5% CO$_2$ and set at 37° C. for 1 h with occasional swirling. Thereafter, the labeled cells were washed three times with PBS and their concentration was finally adjusted to 0.5×10$^6$ cells/ml.

Cytotoxic effector cells were obtained from spleens of C57BL/6J mice previously sensitized with modified or unmodified EL4 as well as ARadLV 136 (see above). Spleens were transferred to petri dishes in a sterile manner in PBS and washed three times with cold PBS. All adhering adipose tissues were teased away with forceps and the spleens were finally minced and crushed with a hub of a 10 ml sterile disposable plastic syringe. Cell suspensions were then transferred to 15 ml conical tubes through 100 μm nylon mesh. Erythrocytes were lysed with ammonium chloride lysing buffer (9 parts 0.16M NH$_4$Cl+1 part 0.17M TRIS pH 7.6; 2 ml/spleen for 1–2 min) and macrophages depleted by incubating cells in dishes for 60 min at 37° C. The cells were then centrifuged and resuspended as before in PBS containing 5% fetal calf serum. Enrichment of T cells was done by incubation of cells with nylon fibers (Fenwall Laboratories, Deerfield, Ill.)

Aliquots of 0.2 ml $^{51}$Cr-labeled target cell suspension containing $10^5$ cells were pipetted into round-bottomed plastic tubes (12×55 mm, Falcon); equal volumes of various dilutions of spleen effector cells were then added to the target cells to yield ratios of lymphocytes to target cells of 50, 10, 2.5 and 1.25. The tubes were then centrifuged at 1000 rpm for 2 min before incubation at 37° C. in a humidified incubator flushed with 5% CO$_2$. After 5 h 0.6 ml PBS was added, the tubes were centrifuged at 1000 rpm for 5 min and 0.5 ml supernatant was collected for counting in a well-type gamma counter (Gammamatic, Kontron). Maximum release was determined by adding 0.6 ml 0.5% NP-40, and spontaneous release was counted from tubes containing labeled target cells alone. The percentage of specific lysis was defined and calculated by the following formula:

$$\text{Specific lysis (\%)} = \frac{\text{experiment }^{51}\text{Cr release} - \text{spontaneous release}}{\text{maximal release} - \text{spontaneous release}} \times 100$$

Lymphocyte proliferation assay

The assay was modified from a procedure described earlier (Vanky et al., 1976. In: Bloom and David, eds., supra). Tumor cells (5×10$^5$), EL4 as well as ARadLV 136, were heavily irradiated (10,000 rad) prior to incubation with an equal numbers of effector cells. Effector cells were prepared from spleen, cleared of erythrocytes and enriched for T cells. The proliferative responses of effector lymphocytes in the presence of inactivated stimulators (tumor cells) were assayed, in triplicate, in round-bottomed 96 -well microtiter plates (Greimer, Labortecknik, FRG). The above mixed cultures were maintained in RPMI-1640 medium containing 5% fetal calf serum, penicillin (100 U/ml), streptomycin (100 μg/ml), sodium pyruvate (1 mM), non-essential amino acids (1%) and 2-mercaptoethanol (5×10$^5$M) for 120 h in a humidified air incubator flushed with 5% CO$_2$. Wells containing stimulators alone served as controls. [$^3$H] Thymidine was pulsed for the last 18 h with 2 μCi [methyl-$^3$H]thymidine (Amersham, UK).

At the end of the incubation period, the plates were centrifuged at 1500 rpm for 10 min and washed once with cold PBS; 0.2 ml ice-cold 10% trichloroacetic acid was then added to the cell pellets. The cells were then harvested using a cell harvestor (Titertek, Flow Laboratories, UK) and automatically transferred to glass-fiber filters. Excess acid was aspirated and washed with 70% ethanol. Washing was repeated twice and the discs punched out in the machine were placed at the bottom of scintillation vials and left to dry overnight at room temperature. Scintillation counting was performed by adding 5 ml scintillation fluid (Instamix/xylene, 4:1) to the vials. Incorporated [$^3$H]thymidine was expressed as cpm±SEM and values that were at least double the controls were considered positive.

Results

DTH assay

The results of the DTH assay are shown in the following Table 1:

TABLE 1

Delayed-type hypersensitivity response to $10^5$ irradiated tumor cells implanted in the right ear of mice primed with treated tumor cells of the same kind

| Prevaccination | R/L $^{125}$IdUrd uptake[a] | |
|---|---|---|
| | EL4 | ARadLV 136 |
| Unprimed | 0.76 ± 0.27 | 0.95 ± 0.09 |
| Primed | | |
| Tumor unmodified | 0.94 ± 0.08 | 1.2 ± 0.12 |
| Tumor + AdA | 1.4 ± 0.12 | 1.2 ± 0.2 |
| Tumor + pressure | 0.94 ± 0.02 | 0.9 ± 0.2 |
| Tumor + pressure + AdA | 2.92 ± 1.60 | 1.3 ± 0.3 |

[a]Results are expressed as means ±SEM of ratio of $^{125}$IdUrd uptake in the right vs the left ear (R/L) obtained in five separate experiments.

The maximal DTH response of the EL4 cells was achieved in mice vaccinated with tumor cells modified by both AdA crosslinking and the application of hydrostatic pressure. A marked increase in DTH reactivity was also seen in mice vaccinated with tumor cells treated with AdA alone. The DTH response after priming with cells modified by pressure treatment only, was essentially the same as after priming with unmodified tumor cells.

Against the relatively strong DTH response obtained with EL4 cells, only a very weak response, as compared to control, was obtained with the ARadLV 136 cells although the priming with cells modified by exposure to both pressure and AdA, showed the strongest response. The mild activity elicited by ARad LV 136 cells is presumably a result of an unidentified non-specific activity.

Histology

Figure 1B:
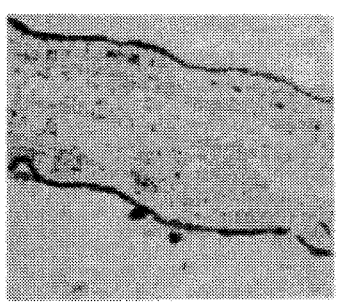
Figure 1C:
Figure 1D:
Figure 1E:

Histological examination of the ears is depicted in FIGS. 1a–1c and as can be seen in this Figure, there is a predominant infiltration of monocytes or macrophages 24 h after the challenge. In ear sections stained with toluidine blue, it was not possible to detect many cells with granules typical of basophils. This indicated that the inflammatory reaction was distinct from cutaneous basophil hypersensitivity.

Cytotoxicity test

Figure 2:
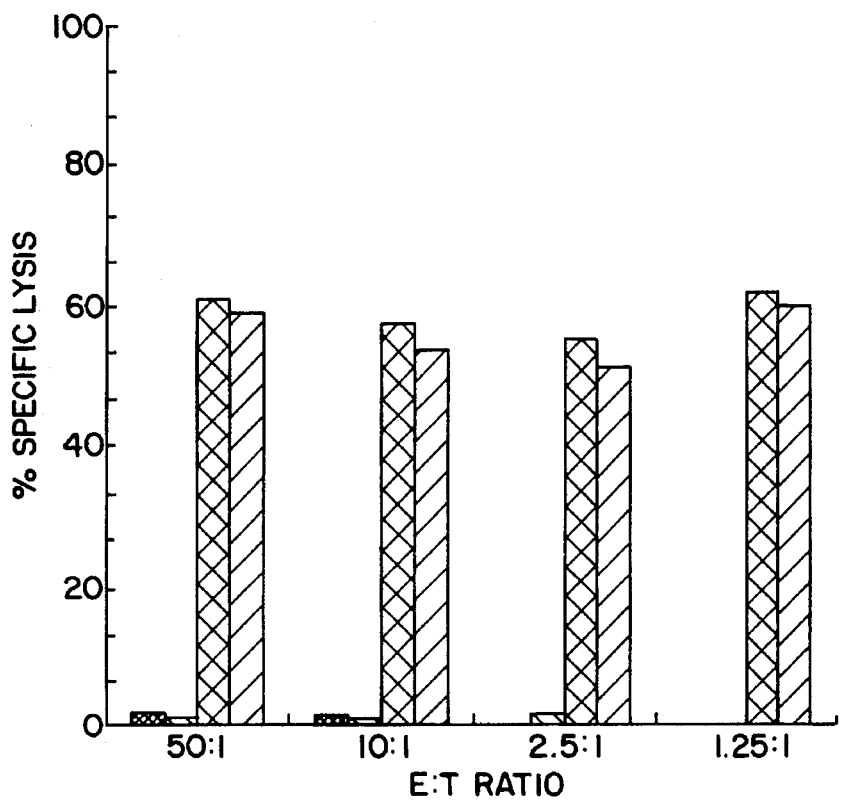
FIG. 2 is a graphic representation of an experiment in which the cytotoxicity of anti-EL4 effector lymphocytes against EL4 target cells at various effector:target (E:T) ratios has been tested, using various anti-EL4 effector lymphocyte preparations obtained from mice treated as follows: non-immunized mice (Treatment I); mice immunized with untreated EL4 cells (Treatment II); mice immunized with AdA-treated EL4 cells (Treatment III); and mice immunized with pressure and AdA-treated EL4 cells (Treatment IV)
Figure 3:
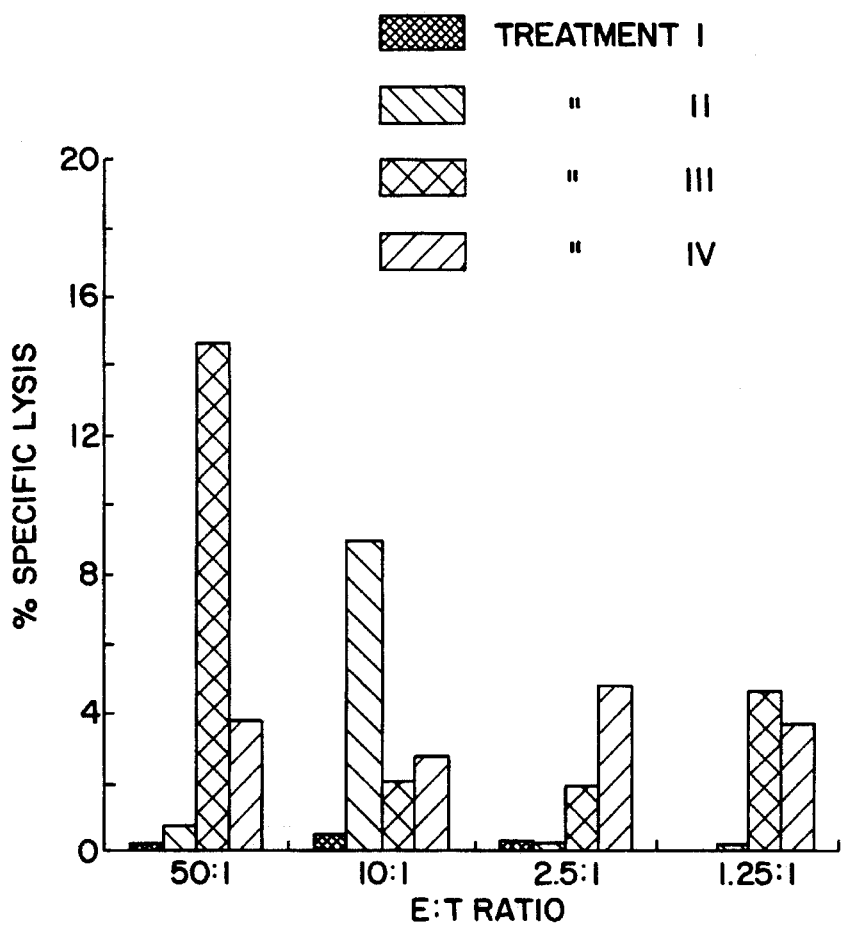
FIG. 3 is a graphic representation of a similar experiment to that shown in FIG. 2 in which the cytotoxicity of anti-ARadLV 136 effector lymphocytes against ARadLV 136 target cells at various effector:target (E:T) ratios has been tested using various anti-ARadLV 136 effector lymphocyte preparations obtained from mice treated as follows: non-immunized mice (Treatment I); mice immunized with untreated ARadLV 136 cells (Treatment II); mice immunized with AdA-treated ARadLV 136 cells (Treatment III); and mice immunized with pressure and AdA-treated ARadLV 136 cells.

The results from the cytotoxicity tests are presented in FIGS. 2 and 3. As seen in these Figures, the cytotoxic ability of anti-EL4 effector cells, isolated from spleens of mice primed with AdA-treated or pressure+AdA-treated tumor cells, to lyse $^{51}$Cr-EL4 targets remain high (≈60%) at all effector:target ratios. Against this, the ability of anti-(ARadLV 136) effector cells to lyse $^{51}$Cr-ARadLV 136 targets was generally low (≈15%) and varied at the different lymphocyte-to-target ratios.

However, it can be seen that with the exception of the 10:1E:T ratio in the experiment with the ARadLV 136 cells, shown in FIG. 2, the cytotoxic effect after immunization with either AdA-treated cells or AdA-pressure-treated tumor cells was much larger than immunization with the other preparations.

Figure 4:
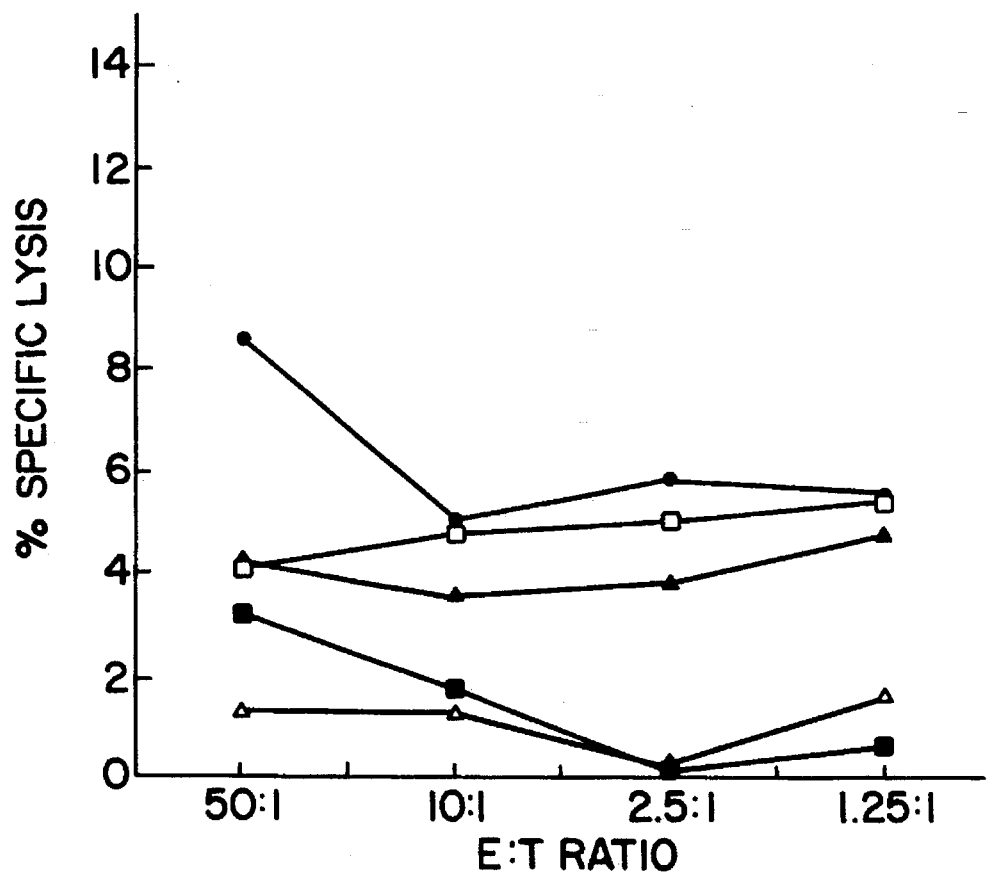
FIG. 4 is a graphic representation of results of a reciprocal assay in which the cross-reactivity of anti-tumor effector lymphocytes has been tested: effector cells—from mice immunized with pressure and AdA-treated ARadLV 136 cells, target cells—EL4 (filled circle); effector cells—obtained from mice immunized with untreated EL4 cells, target cells—ARadLV 136 (empty triangle); effector cells—obtained from mice immunized with AdA-treated EL4 cells, target cells—ARadLV 136 (filled triangle); effector cells—AdA-treated ARadLV 136 cells, target cells—EL4 (filled squares); effector cells—AdA and pressure-treated EL4 cells, target cells—ARadLV 136 (empty squares)

In order to investigate the specific nature of tumorcell lysis, the effectors, anti-EL4 as well as anti-ARadLV 136 were tested in a reciprocal manner, i.e. anti-EL4 vs. $^{51}$CrARadLV 136 and vice versa and results are shown in FIG. 4. Target lysis in these experiments were low and insignificant (4%–8%) as compared to the direct assays in either tumor systems as shown in FIGS. 2 and 3. These results suggest high degree of specific recognition.

Lymphocyte proliferation

Results of [$^3$H]thymidine uptake in the 5-day mixed cultures are presented in the following Tables 2 and 3.

TABLE 2

Proliferation of anti-EL4 lymphocytes in vitro co-cultured with three different tumor cells[a]

| Effector spleen source | Zero stimulation control | Irradiated EL4 (H-2k[b]) | Irradiated ARLV 136 (H-2k[b]) | Irradiated P815 (H-2k[d]) |
|---|---|---|---|---|
| Naive mice | 360 ± 150 | 220 ± 100 | 600 ± 240 | 400 ± 160 |
| Primed mice | | | | |
| Unmodified tumor | 260 ± 106 | 18790 ± 660 (74) | 125464 ± 5001 (483) | 36476 ± 1390 (141) |
| AdA-treated tumor | 270 ± 110 | 167420 ± 6726 (621) | 45454 ± 1737 (169) | BL |
| Pressure-treated tumor | 410 ± 160 | 107980 ± 4256 (264) | 93314 ± 3654 (335) | BL |
| Pressure + AdA-treated tumor | 280 ± 114 | 313510 ± 12672 (742) | 207444 ± 8383 (742) | BL |

[a]Expressed as cpm ± SEM incorporated [$^3$H]thymidine.
[b]Figures in parentheses indicate stimulation index values as means of triplicate stimulated and unstimulated cultures.
[d]BL = background level

TABLE 3

Proliferation of anti-ARadLV 136 lymphocytes in vitro co-cultured with three different tumor cells[a]

| Effector spleen source | Zero stimulation control | Irradiated ARLV 136 (H-2k[b]) | Irradiated EL4 (H-2k[b]) | Irradiated P815 (H-2k[d]) |
|---|---|---|---|---|
| Naive mice | 400 ± 160 | 600 ± 240 | 220 ± 100 | 400 ± 160 |
| Primed mice | | | | |
| Unmodified tumor | 590 ± 240 | 17924 ± 407 (32) | 58400 ± 2166 (98) | 101306 ± 3920 (180) |
| AdA-treated tumor | 500 ± 200 | 106000 ± 3930 (213) | 40090 ± 1446 (81) | 2826 ± 20 (8) |
| Pressure-treated tumor | 650 ± 260 | 70250 ± 2420 (109) | 74100 ± 2786 (116) | BL |
| Pressure + AdA-treated tumor | 770 ± 190 | 194230 ± 7540 (253) | 54820 ± 2056 (73) | BL |

[a]Expressed as cpm ± CEM incorporated [$^3$H]thymidine.
[b]Figures in parentheses indicate stimulation index values as means of triplicate stimulated and unstimulated cultures.
[d]BL = background level The above results show that the proliferative capacity of anti-EL4 effector cells against syngeneic and allogeneic targets shows high incorporation of the label when grown in the presence of the syngeneic target EL4, while moderate proliferation was seen for the irrelevant H-2-identical (ARadLV 136), and H-2-disparate (P815) target cells. Similar responses were noted for anti-ARadLV 136 effector proliferation in the presence of syngeneic ARadLV 136, H-2-identical (EL4) and H-2-disparate (P815) targets.

Additionally, the above results clearly show that proliferation of anti-tumor effector cells in the presence of the relevant tumor was considerably enhanced in the groups treated with AdA, with pressure or with AdA plus pressure.

Example 2

In the experiments of this Example, the viability of C57B1 mice challenged with $10^5$ viable untreated tumor cells following pretreatment with various immunogenic preparations was tested. Survival after challenge was scored at day 30.

The pretreatment consisted of two vaccinations, one three weeks and the other one week prior to the challenge, with an immunogenic preparation which consisted of cells subjected to one of the following modification treatments: exposure to AdA, application of hydrostatic pressure or a combination of the two, following essentially the same procedure as described above in Example 1. The cells used for vaccination were of the same kind as the cells used to challenge the mice.

The cells used in this experiment were either EL-4 (see Example 1) or BL6 melanoma cells which are a very invasive variant of the B16 cell line (Hart 1979, Am. J. Patholog. 97:587). The B16-BL6 tumor was serially passaged in syngeneic C57B1 mice by s.c. inoculation of 2–5×$10^6$ cells.

Test No. 1

Four groups of mice were used, each pretreated with one of the following preparations:

Group 1: EL-4 leukemia cells treated for 10 minutes by various levels of hydrostatic pressure, in the presence of 40 mM AdA;

Group 2: EL-4 leukemia cells treated for 10 minutes by various levels of hydrostatic pressure and then by 40 mMAdA;

Group 3: B16 melanoma cells treated as Group 1;

Group 4: B16 melanoma cells treated as Group 2.

Figure 5:
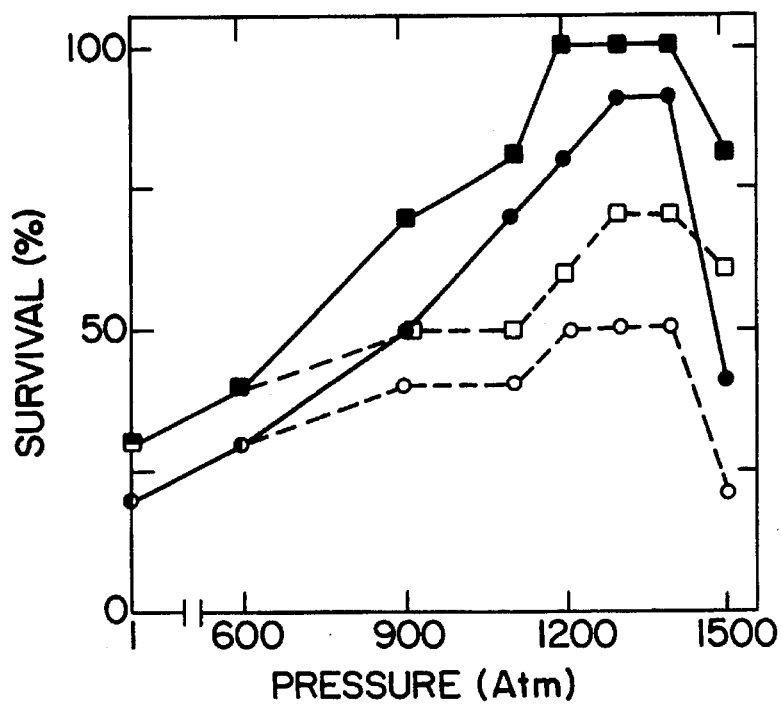
FIG. 5 is a graphic representation of an experiment in which the survivability of mice challenged with tumor cells after immunization with one of the following preparations was tested: EL4 cells treated with various levels of hydrostatic pressure in the presence of 40 mM AdA (filled squares); EL4 cells treated with increasing level of hydrostatic pressure and then with 40 mM AdA (empty squares); B16 melanoma cells treated by various levels of hydrostatic pressure in the presence of 40 mM AdA (filled circles) and B16 melanoma cells treated with hydrostatic pressure and then with 40 mM AdA.

The results are shown in FIG. 5 (each point represents an average of 10 animals): Group 1—filled squares; Group 2—empty squares; Group 3—filled circles; Group 4—empty circles.

The results demonstrate that the maximal survivability was obtained after vaccination with an immunogenic preparation exposed to a hydrostatic pressure of 1200–1400 and surprisingly far inferior results were obtained after exposure to hydrostatic pressure of 1500 atm. Furthermore, these results show that the simultaneous exposure to both hydrostatic pressure and AdA leads to a higher survivability of the mice than these two treatments in sequence.

Test No. 2

Several groups of C57B1 mice (10 mice in each group) were pretreated by one of the following preparations:

Treatment 1: EL-4 leukemia cells treated for 10 minutes by hydrostatic pressure of 1350 atm in the presence of various increasing concentrations of AdA;

Treatment 2: B16 melanoma cells treated as in Treatment 1.

Treatment 3: B16 melanoma cells treated for 10 min. by hydrostatic pressure of 1350 atm in the presence of various concentrations of AMPdA.

Figure 6:
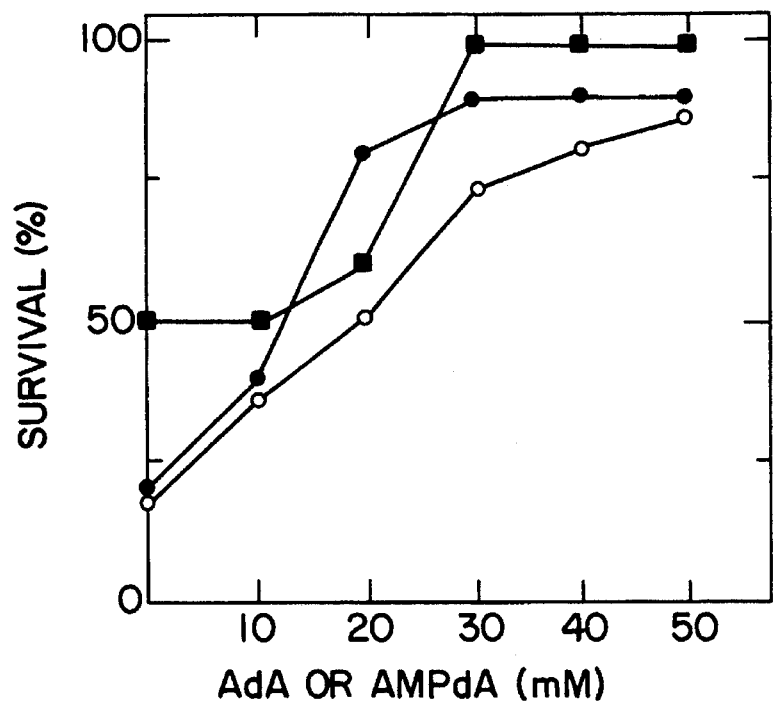
FIG. 6 shows the survivability of mice challenged with tumor cells following immunization with one of the following preparations: EL4 leukemia cells treated for 10 min with hydrostatic pressure of 1350 atm in the presence of various concentrations of AdA (filled squares); B16 melanoma cells treated in the same manner (filled circles); B16 melanoma cells treated in the same manner with AMPdA (empty circles)

The results of the experiments are shown in FIG. 6 (each point represents an average of 10 animals): Treatment 1—filled squares; Treatment 2—filled circles; Treatment 3—empty circles.

As can be clearly seen the maximal survival rate was obtained with an AdA or AMPdA concentration of above 30 mM.

Test No. 3

Five groups of C57B1 mice (6 mice in each group) were immunized subcutaneously and then challenged with B16-BL6 cells. The preparation used for immunization consisted of plasma membranes isolated by discontinuous sucrose gradient centrifugation (Maeda et al., 1983, Biochim. Biosphys. Acta 731:115) from untreated or treated cells. Details of the immunizing preparations is given in Table 4.

The following parameters were tested for each group of animals: survival rate; mean tumor diameter, measured using standard callipers in three orthogonal directions and presented by the mean value; metastatic nodules in lungs, scored after removal of the lungs, and fixations with Bouin's fixative and then washing with 70% ethanol. The results of this experiment are also shown in the following Table 4.

TABLE 4

| Immunized s.c. on day −7 with: | Immunized s.c. on day 0 and 1 with: | Challenged on day 3 s.c. with: | Survivors Total | Mean Tumor Diameter (mm) | Metastatic Nodules in lungs |
|---|---|---|---|---|---|
| 1. Nothing | Nothing | $10^5$ B16 | 0/6 | >25 | 35–40 |
| 2. Nothing | Plasma membranes from untreated B16 (0.1 mg protein) | $10^5$ B16 | 1/6 | 14 ± 2.2 | 10–15 |
| 3. Plasma membranes from untreated B16 (0.1 mg protein) | Plasma membranes from untreated B16 (0.1 mg protein) | $10^5$ B16 | 2/6 | 7 ± 3.1 | 6–9 |
| 4. Nothing | Plasma membranes from modified B16 (0.1 mg protein) | $10^5$ B16 | 5/6 | 6 ± 0.8 | None |
| 5. Plasma membranes from modified B16 (0.1 mg protein) | Plasma membranes from modified B16 (0.1 mg protein) | $10^5$ B16 | 6/6 | 3.5 ± 0.3 | None |

*All modifications on B16-BL6 melanoma consisted of simultaneous treatment of tumor cells with 40 mM AdA and 1350 atm hydrostatic pressure.

These results demonstrate that immunization with an immunizing preparation consisting of plasma membranes isolated from B16-BL6 cells treated by pressure and AdA in accordance with the invention (Treatments 4 and 5) brought a very high survival rate, the mean tumor diameter was minimal and no metastatic nodules in the lungs were observed.

These results prove the unexpected high potency of the vaccination treatment of the invention.

Example 3

The presence of MHC class I antigens (H-2k$^b$) and the tumor-specific retroviral antigen on B16-BL6 melanoma cells, derived from s.c. tumors either directly after obtaining single cell suspensions or passaging the cells in culture 6–8 times over a period of 3–4 weeks, was analyzed by flow cytometry.

About $10^6$ modified or unmodified B16-BL6 tumor cells were incubated as a first step with unlabelled primary antibodies: 30 μl (25 μg) of anti-class I monoclonal antibody (clone 28-8-6, obtained from Dr. D. Sachs, National Cancer Institute, U.S.A.) or 10 μl (8 μg) of monoclonal antibody against a retroviral antigen on the surface of B16 cells (MM2.9B6, Leong et al. 1988, Cancer Res. 48:4954) in a final volume of 50 μl containing 1% FCS (fetal calf serum) and 0.01% of sodium azide and incubated for 45 minutes at 4° C. Cells were washed twice in HBS (hepes buffered saline) and the pellet was resuspended in a solution of a labeled secondary antibody: 50 μl of a solution containing 40 μg of the F(ab')2 fragment of FITC-GAMIG (fluorescein isothiocyanate labeled goat anti-mouse IgG) in HBS with 1% FCS and 0.1% sodium azide and incubated for an additional 45 minutes at 4° C. in the dark. Thereafter cells were washed as before and fixed in 1% freshly prepared paraformaldelyde for 20 minutes. Fixed cells were washed thrice in HBS, resuspended in 0.5 ml HBS and passed through 100μ nylon mesh prior to flow cytometric analysis. Samples were stored for no more than 24 hours in the dark at 4° C. as samples stored for longer period gave rise to high autofluorescence.

Non-reacted B16-BL6 cells and B16-BL6 cells which reacted directly with FITC-GAMIG, and 2% BSA (bovine serum albumin) served as negative controls. Modified as well as unmodified cells were labeled and analyzed on either FACS 440 (Becton-Dickinson, Mountainview, Calif.) or on the FACScan instrument (Becton-Dickinson). Populations which were 10 determined as positive on dual parameter (forward and orthogonal light scatter) analysis were gated and data was acquired on live gates. Histograms were generated using either consort 40 software on FACS 440 or consort 30 with LYSYS software available with FACScan. Appropriate controls were introduced in order to apply logic threshold values. Amelanotic cells which appeared in the population were gated out in the present analysis by light scatter gating. Approximately 10,000 events were tested in each sample.

Exposure to AdA or to hydrostatic pressure was carried out in a similar manner to that described in Example 1.

Figure 7A:
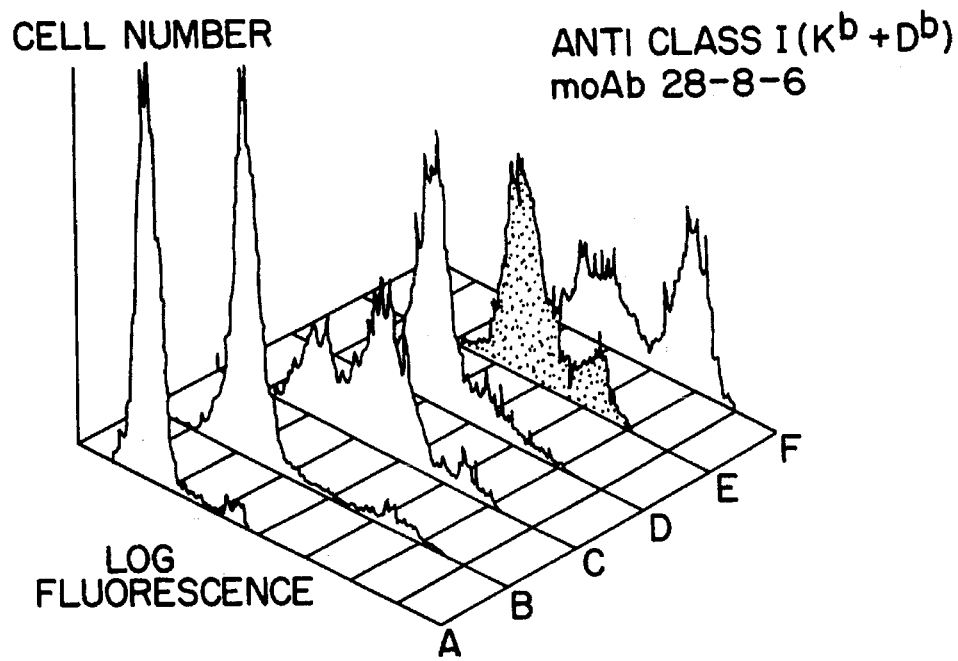
FIGS. 7a and 7b show a three-dimensional overlay of antigen expression on B16-BL6 melanoma cell plasma membrane surface as analyzed on FACScan by indirect immunofluorescence: A & B —negative controls (A—autofluorescence; B—cells reacted only with secondary antibody); C—unmodified cells; D & X—cells exposed to 20 mM AdA; E & Z—cells exposed to hydrostatic pressure of 1,200 atm for 15 minutes; F & Y—cells exposed simultaneously to both 20 mMAdA and 1,200 atm pressure.
Figure 7B:
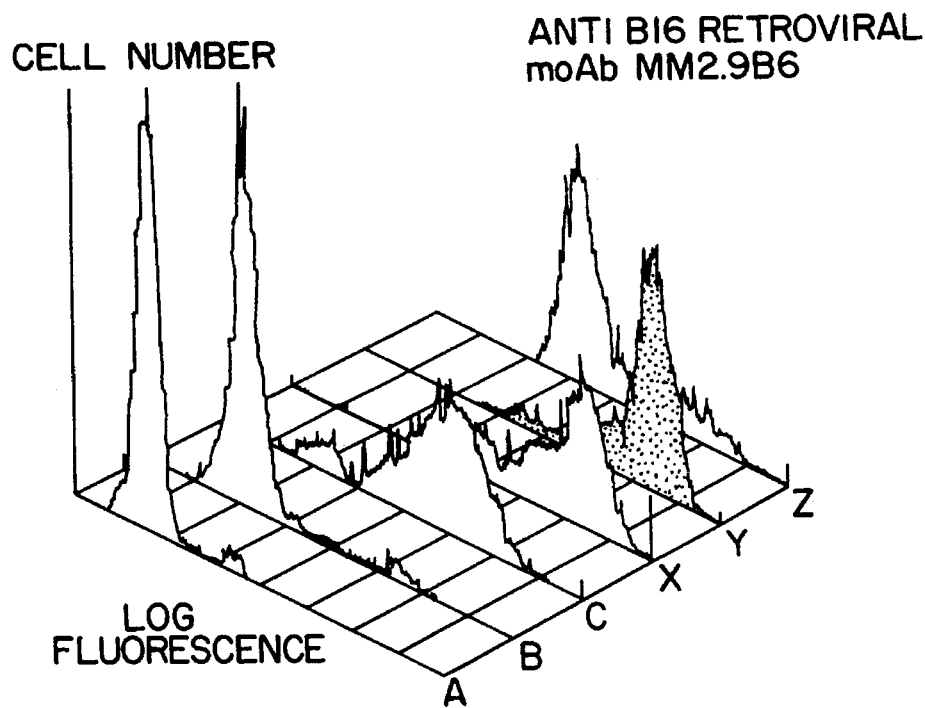

As can be seen in FIGS. 7a and 7b, maximum expression of both class I and melanoma-specific antigen was noted with B16-BL6 cells which were modified by 1,200 atmospheres of hydrostatic pressure and simultaneous crosslinking with 20 mM AdA.

Figure 8:
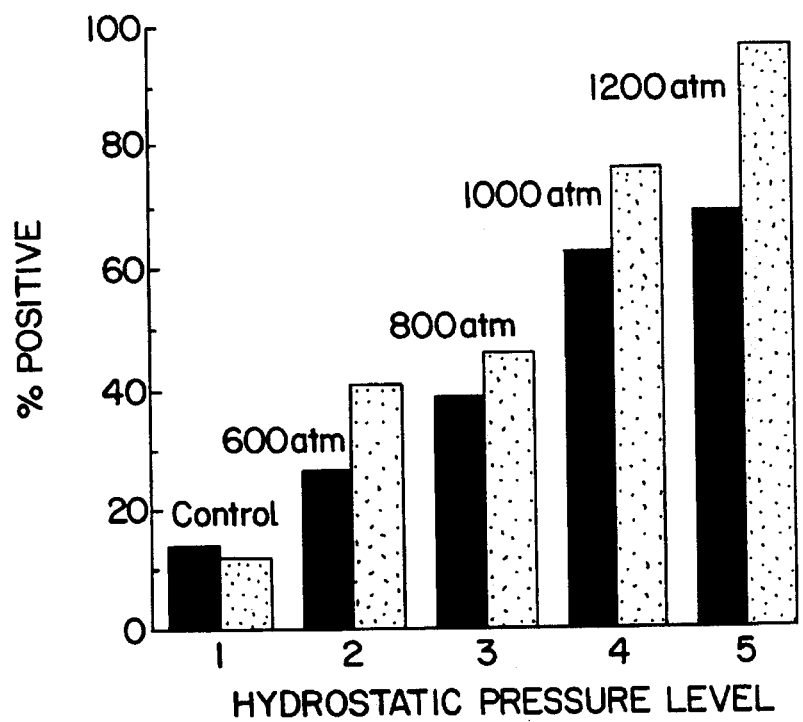
FIG. 8 shows the effect (as per cent of positive cells counted by FACScan instrument out of 10,000 events) of graded levels of hydrostatic pressure (applied for 15 minutes) combined with a constant dose of AdA 20 mM on antigen expression in B16-BL6 melanoma cells: filled bars—class I antigen, gray bars—B16 antigen.
Figure 9:
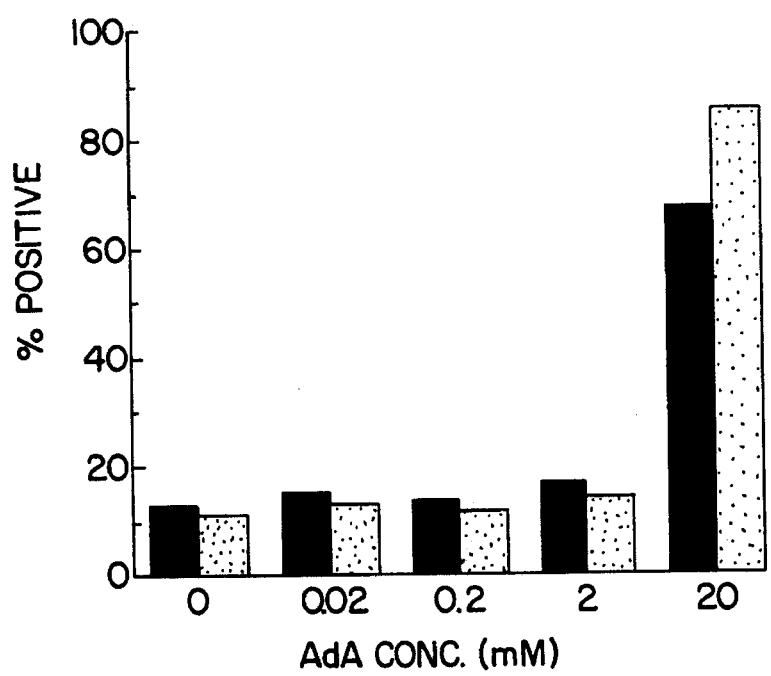
FIG. 9 shows the effect (per cent positive as determined on FACScan out of 10,000 events) of varying concentrations of AdA combined with a constant level of hydrostatic pressure (1200 atm, 15 minutes) on antigen expression in B16-B16 melanoma cells: black bars—MHC class I antigen, gray bars B16 antigen.

In another set of experiments B16-BL6 cells were exposed to hydrostatic pressure in the range of 600–1,200 atm and to a constant concentration of AdA of 20 mM and the results are shown in FIG. 8. In a further experiment B16-BL6 cells were exposed to a constant level of 1,200 atm of hydrostatic pressure while incubation with AdA at concentrations from 0.002 mM to 20 mM, and the results are shown in FIG. 9. As can be seen in these Figures, maximum fluorescent intensity for both class I and B16-BL6 tumor antigen was observed with the combination of a high level of pressure (1,200 atm) and the highest in the series of concentrations of AdA, 20 mM.

I claim:

1. A vaccine preparation capable of inducing an anti-tumor immune response comprising a pharmaceutically acceptable carrier and an anti-tumor immune response-inducing effective amount of an immunogenic preparation comprising modified tumor cells or plasma membranes obtained therefrom; wherein said modified tumor cells are prepared by exposing isolated tumor cells to a crosslinking effective concentration of a 2',3'-nucleoside or nucleotide dialdehyde cross linking agent at the same time that said cells are subjected to hydrostatic pressure of from 1,200 to 1,400 atmospheres for a time sufficient to cause modification of the plasma membranes of said tumor cells.

2. Modified tumor cells, or plasma membranes obtained therefrom, capable of inducing an anti-tumor immune response, wherein said modified tumor cells or plasma membranes are prepared by exposing tumor cells to a 2',3'-nucleoside or nucleotide dialdehyde crosslinking agent at a crosslinking effective concentration at the same time that said tumor cells are subjected to hydrostatic pressure at a level of from 1,200 to 1,400 atmospheres for a time sufficient to cause modification of the plasma membranes of said tumor cells.

3. The cells according to claim 2, wherein said crosslinking agent is represented by the following formula I:

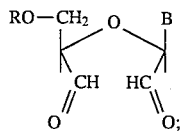

wherein, R is H or a mono-, di-, or tri-phosphate group; and B is a base selected from the group consisting of adenine, guanine, cytosine, thymine, and uracil.

4. The cells according to claim 3, wherein said crosslinking agent is 2',3'-adenosine dialdehyde (AdA) or 2',3'-adenosine monophosphate dialdehyde (AMPdA).

5. The cells according to claim 2, wherein said crosslinking agent is at a concentration of 20 mM.

6. The cells according to claim 4, wherein said crosslinking agent is at a concentration of 20 mM.

7. The cells according to claim 3, wherein said crosslinking agent is at a concentration of 20 mM.

8. The cells according to claim 2, wherein said modified tumor cells are prepared by exposing said tumor cells to 2',3'-adenosine dialdehyde (AdA) or 2', 3'-adenosine monophosphate dialdehyde (AMPdA) crosslinking agent at a concentration of 20 mM at the same time that said cells are subjected to said hydrostatic pressure of from about 1,200 to 1,400 atmospheres.

9. Plasma membranes derived from modified tumor cells according to claim 2.

10. Plasma membranes derived from modified tumor cells according to claim 3.

11. Plasma membranes derived from modified tumor cells according to claim 4.

12. Plasma membranes derived from modified tumor cells according to claim 5.

13. Plasma membranes derived from modified tumor cells according to claim 6.

14. Plasma membranes derived from modified tumor cells according to claim 7.

15. Plasma membranes derived from modified tumor cells according to claim 8.

16. An immunogenic preparation comprising modified tumor cells according to claim 2, and a pharmaceutically acceptable carrier.

17. An immunogenic preparation comprising modified tumor cells according to claim 3, and a pharmaceutically acceptable carrier.

18. An immunogenic preparation comprising modified tumor cells according to claim 4, and a pharmaceutically acceptable carrier.

19. An immunogenic preparation comprising modified tumor cells according to claim 5, and a pharmaceutically acceptable carrier.

20. An immunogenic preparation comprising modified tumor cells according to claim 6, and a pharmaceutically acceptable carrier.

21. An immunogenic preparation comprising modified tumor cells according to claim 7, and a pharmaceutically acceptable carrier.

22. An immunogenic preparation comprising modified tumor cells according to claim 8, and a pharmaceutically acceptable carrier.

23. An immunogenic preparation comprising plasma membranes according to claim 9, and a pharmaceutically acceptable carrier.

24. An immunogenic preparation comprising plasma membranes according to claim 10, and a pharmaceutically acceptable carrier.

25. An immunogenic preparation comprising plasma membranes according to claim 11, and a pharmaceutically acceptable carrier.

26. An immunogenic preparation comprising plasma membranes according to claim 12, and a pharmaceutically acceptable carrier.

27. An immunogenic preparation comprising plasma membranes according to claim 13, and a pharmaceutically acceptable carrier.

28. An immunogenic preparation comprising plasma membranes according to claim 14, and a pharmaceutically acceptable carrier.

29. An immunogen derived from modified tumor cells or plasma membranes thereof, wherein said modified tumor cells are capable of inducing an anti-tumor immune response and are prepared by exposing isolated tumor cells to a crosslinking effective concentration of a 2',3'-nucleoside or nucleotide dialdehyde crosslinking agent at the same time that said tumor cells are subjected to hydrostatic pressure of from 1,200 to 1,400 atmospheres for a time sufficient to cause modification of the plasma membranes of said tumor cells.

30. The immunogen according to claim 29, wherein said crosslinking agent is represented by the following formula I:

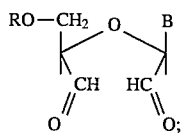

wherein, R is H or a mono-, di-, or tri-phosphate group; and B is a base selected from the group consisting of adenine, guanine, cytosine, thymine, and uracil.

31. The immunogen according to claim 29, wherein said crosslinking agent is 2',3'-adenosine dialdehyde (AdA) or 2',3'-adenosine monophosphate dialdehyde (AMPdA).

32. The immunogen according to claim 29, wherein said crosslinking agent is at a concentration of 20 mM.

33. The immunogen according to claim 29, wherein said modified tumor cells are prepared by exposing tumor cells to said crosslinking agent at a concentration of 20 mM at the same time as said tumor cells are subjected to said hydrostatic pressure at a level of about 1,200 to 1,400 atmospheres.

34. A process for preparing an immunogen derived from modified tumor cells, said immunogen being capable of inducing an anti-tumor immune response, comprising the steps of:

(a) providing tumor cells;

(b) incubating said tumor cells with a crosslinking effective concentration of a crosslinking agent represented by the following formula I:

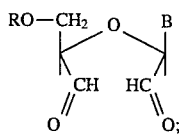

wherein, R is H or a mono-, di-, or tri-phosphate group; and B is a base selected from the group consisting of adenine, guanine, cytosine, thymine, and uracil for a time sufficient to obtain crosslinking of cellular membrane proteins, at the same time that said cells are subjected to hydrostatic pressure of from 1,200 to 1,400 atmospheres; and (d) removing unbound crosslinking agent.

35. The process according to claim 34, wherein in step (b), said crosslinking agent is a 2',3'-nucleoside or nucleotide dialdehyde.

36. The process according to claim 35, wherein said cross linking agent is 2',3'-adenosine dialdehyde (AdA) or 2',3'-adenosine monophosphate dialdehyde (AMPdA).

37. The vaccine preparation according to claim 17, wherein said tumor cells are exposed to 2',3'-adenosine dialdehyde (AdA) or 2',3'-adenosine monophosphate dialdehyde (AMPdA) crosslinking agent at the same time that said tumor cells are subjected to hydrostatic pressure of from about 1,200 to 1,400 atmospheres.

38. A method of inducing an anti-tumor immune response in a subject, comprising administering to said subject an effective amount of the immunogen according to any one of claims 29, 30, 31, 32, or 33.

39. A method of inducing an anti-tumor immune response in a subject, comprising administering to said subject an effective amount of the immunogen according to claim 29, claim 30, or claim 31.

40. A method of inducing an anti-tumor immune response in an individual having a tumor growth, said method comprising the steps of:

(a) withdrawing at least a portion of said tumor growth from said individual by biopsy or surgery;

(b) dissociating intact tumor cells by mechanical or enzymatic means;

(c) dispersing said tumor cells in a medium;

(d) incubating said tumor cells with a crosslinking effective amount of 2',3'-adenosine dialdehyde or 2', 3'-adenosine monophosphate dialdehyde at the same time that said cells are subjected to hydrostatic pressure of from 1,200 to 1,400 atmospheres for a time sufficient to cause modification of the plasma membranes of said tumor cells;

(e) removing unbound 2',3'-adenosine dialdehyde or 2',3'-adenosine monophosphate dialdehyde;

(f) preparing an immunogen derived from said modified crosslinked and pressure treated cells; and (g) injecting said modified tumor cell immunogen into said individual so as to induce an anti-tumor immune response.

41. A method of treating a patient to induce an anti-tumor immune response, comprising the steps of:

(a) withdrawing immune cells from said patient;

(b) culturing said immune cells with a tumor cell immunogen derived from modified tumor cells; wherein said modified tumor cells are prepared by:

(i) providing at least a portion of a tumor growth;

(ii) dissociating tumor cells from said growth by mechanical or chemical means;

(iii) exposing said tumor cells to a crosslinking effective amount of a 2', 3'-nucleoside or nucleotide dialdehyde at the same time that said tumor cells are subjected to hydrostatic pressure of from 1,200 to 1,400 atmospheres;

wherein said culturing is for a time sufficient to cause said patient's immune cells to become reactive against said modified tumor cells;

(c) isolating said cultured and anti-tumor cell reactive immune cells; and (d) injecting said cultured and reactive immune cells into said patient so as to induce an anti-tumor immune response in said patient.

42. The method according to claim 38, wherein said crosslinking agent is 2',3'-adenosine dialdehyde (AdA) or 2',3'-adenosine monophosphate dialdehyde (AMPdA).

43. The method according to claim 41, wherein said crosslinking agent is 2',3'-adenosine dialdehyde (AdA) or 2',3'-adenosine monophosphate dialdehyde (AMPdA).

44. The method according to claims 29, 30, 32, or 33, wherein said tumor cells are exposed to 2',3'-adenosine dialdehyde (AdA) or 2',3'-adenosine monophosphate dialdehyde (AMPdA) crosslinking agent at the same time that said tumor cells are subjected to hydrostatic pressure of from about 1,200 to 1,400 atmospheres.

\* \* \* \* \*